United States Patent [19]

Nakatani et al.

[11] 4,420,500

[45] Dec. 13, 1983

[54] COMPOSITION AND PROCESS FOR PREPARING TRANSPARENT CONDUCTING FILM

[75] Inventors: Mitsuo Nakatani, Yokohama; Mitsuo Yamazaki, Hitachi; Masaaki Okunaka, Fujisawa; Ryoichi Sudo, Yokosuka; Kenji Tochigi, Yokohama; Hitoshi Yokono, Katsuta, all of Japan

[73] Assignees: Hitachi, Ltd.; Hitachi Chemical Co., Ltd., both of Tokyo, Japan

[21] Appl. No.: 344,973

[22] Filed: Feb. 2, 1982

[30] Foreign Application Priority Data

Feb. 20, 1981 [JP] Japan ................................ 56-23111

[51] Int. Cl.³ .................... B05D 3/02; B05D 3/06; H01B 1/06
[52] U.S. Cl. .................... 427/54.1; 252/521; 252/518; 427/108; 427/161; 427/380
[58] Field of Search ............ 427/54.1, 108, 380, 427/161; 252/518, 521

[56] References Cited

FOREIGN PATENT DOCUMENTS 2021083 11/1979 United Kingdom ................ 427/108

*Primary Examiner*—Michael R. Lusignan
*Attorney, Agent, or Firm*—Antonelli, Terry & Wands

[57] ABSTRACT

A transparent conducting film is prepared from a composition comprising an indium compound, a tin compound, and a solvent as essential components, the tin compound being a compound represented by the following general formula:

$$(R)_a Sn(NO_3)_b (X)_{4-a-b} \tag{I}$$

wherein R is an alkyl group having 1 to 4 carbon atoms, X is a hydroxyl group, a halogen atom, or a carboxyl group, and a and b are integers of 1~3, and a+b≦4 by coating a substrate with the said composition, subjecting the coated substrate to ultraviolet irradiation at a substrate temperature of 200° C. or higher, and heating the substrate at 400° C. or higher. The composition has a long pot life and the film has a low resistance and distinguished mechanical strength, chemical resistance and etching susceptibility.

27 Claims, 1 Drawing Figure

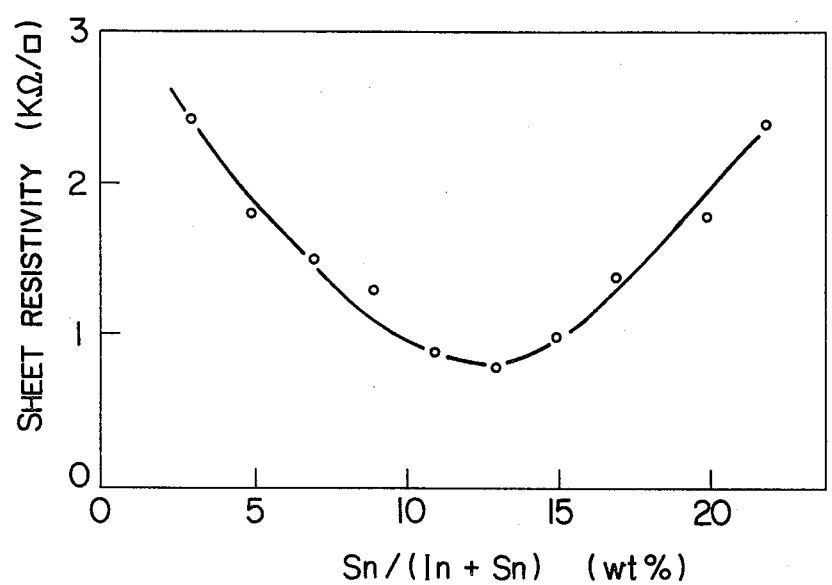

COMPOSITION AND PROCESS FOR PREPARING TRANSPARENT CONDUCTING FILM

BACKGROUND OF THE INVENTION

1. Field of the Invention

The present invention relates to a composition and a process for preparing a transparent conducting film on substrates of glass, ceramics, etc.

2. Brief Description of the Prior Art

The transparent conducting film is widely utilized as electrodes for liquid crystal display devices, electrochromic devices, EL, photosemiconductors, etc., and further as non-fogging exothermic resistors for automobiles, airplanes, etc.

It is known to prepare the transparent conducting film by coating a substrate with a solution containing an indium compound and a tin compound by dipping, spinner coating, brush coating, printing, etc., and heat-treating the coated substrate, thereby thermally decomposing the organic components and forming an oxide film of indium and tin.

The well known solution containing an indium compound and a tin compound includes (1) a coating solution containing a fluorine-containing indium compound such as basic indium trifluoroacetate, and stannic chloride, (2) a coating solution containing indium chloride and stannic chloride, (3) a coating solution containing an alkoxy indium or indium carboxylate, and an alkoxy stannous compound or stannous carboxylate, (4) a coating solution containing indium naphthenate and tin octylate, and (5) a coating solution containing indium nitrate dissolved in β-diketone or a mixed solution of β-diketone with other solvent and tin halide (stannous chloride, stannic chloride, stannous bromide, stannic bromide, stannous iodide, or stannic iodide) or tin nitrate or tin acetate.

However, as a result of investigations of characteristics of films obtained by applying these coating solutions onto soda glass substrates each having a silicon oxide film (thickness: about 2,000 Å) on the surfaces and firing the substrates at 500° C., substantial upper limit temperature giving no deformation to the soda glass, for one hour, it was found that these coating solutions had the following problems. The film obtained from the solution (1) had a high resistance, the one obtained from the solution (2) had a white turbid state and also had a high resistance, the ones obtained from the solutions (3) and (4) had a little lower but not satisfactory resistance then those of the films obtained from the solutions (1) and (2), and the resistance was liable to fluctuate greatly with a slight change in film-forming conditions (for example, a slight change in temperature and humidity at the site of coating, drying and calcining conditions for the coated film, etc.). That is, it was difficult to obtain a film of low resistance with stability. Furthermore, the film suffered from such disadvantages as low mechanical strength and high chances to damages.

The film obtained from the solution (5) had relatively better characteristics, but had still higher resistance. The resistance was liable to fluctuate greatly with a slight change in the film-forming conditions. The stability of the solution with time was poor, and the resistance of the resulting film was increased within 10 to 20 days after application even by using the coating solution at room temperature (23° to 25° C.).

It is obvious from the foregoing that the coating solutions so far known cannot produce a transparent conducting film having a good light transmission, a low resistance and good mechanical strength without any white turbid state with stability.

SUMMARY OF THE INVENTION

An object of the present invention is to provide a composition and a process for preparing a transparent conducting film free from the disadvantages of the prior art.

The object of the present invention can be attained by using a tin compound represented by the following general formula (1) in a composition containing an indium compound, a tin compound and a solvent as essential components.

$$R_a Sn(NO_3)_b (Z)_{4-a-b} \quad (1)$$

wherein R is an alkyl group having 1–4 carbon atoms, Z is a hydroxyl group, halogen atom, or carboxyl group, and a and b are integers of 1 to 3 and $a+b \leq 4$.

The present invention resulted from extensive studies of coating compositions based on various combinations of indium compounds, tin compounds and solvents. That is, it was found that (1) species of tin compound for use in a coating solution had a great influence upon the stability of the coating solution with time, characteristics of the resulting transparent conducting film, and the reproducibility of the characteristics, (2) the so far well known tin compounds such as tin halides, for examples, stannous chloride, stannic chloride, stannous bromide, stannic bromide, stannous iodide, stannic iodide, etc., when used in a coating solution produced a transparent conducting film having a high resistance, and poor reproducibility of film characteristics, also providing a coating solution having a poor stability with time, (3) stannous carboxylate, one of the so far well known tin compounds, for example, tin octylate, tin butyrate, etc. when used in a coating solution, could produce a transparent conducting film having a lower resistance than when the tin halides are used, but the stability of the coating solution with time and the reproducibility of the film characteristics were poor as in the case of using the tin halides, and (4) the so far well known alkoxy stannous compounds had a poor solubility in a solvent, so that no substantial homogeneous composition could be obtained, and, as a result of further extensive studies of various tin compounds, it was newly found that (5) an alkyl tin nitrate of the present invention could produce a distinguished coating solution having excellent characteristics without any of the foregoing problems. It seems that the high resistance of a transparent conducting film obtained from a coating solution containing tin halide is due to vaporization of the tin halide at the firing of the coated film or due to the halogen remaining in the film. It seems that the poor stability with time of a coating solution containing the tin halide or the stannous carboxylate is due to the fact that these tin compounds slowly react with $H_2O$ in the coating solution (there is a small amount of $H_2O$ in a coating solution because the solvent used in the coating solution is a polar solvent which is hygroscopic) to form hydroxy tin compounds having a low solubility, thereby deteriorating the characteristics of the resulting transparent conducting film, and further that the tin compounds undergo dissociation and slowly react with other components (for example, organic components of indium compound), thereby changing the composition of the coating solution.

Also, it seems that the poor reproducibility of the resulting film characteristics is due to the fact that the coating film applied to the substrate absorbs $H_2O$ from the air, reaction takes place between the tin compound and $H_2O$ in the coating film, and consequently the characteristics of the transparent conducting film obtained by firing are liable to fluctuate.

On the other hand, the alkyl tin nitrate has an alkyl group and thus has a good solubility in an organic solvent. Furthermore, the alkyl group is non-dissociable, and thus very stable, and the alkyl tin nitrate is readily heat-decomposable due to its nitrate group, so that a transparent conducting film having a low resistance and a high strength can be obtained.

In the present composition for producing a transparent conducting film, a mixing ratio of an alkyl tin nitrate to the alkyl tin nitrate plus an indium compound is 5–20% in terms of $Sn/(In+Sn) \times 100$, particularly preferably 8–15%. If the mixing ratio is below 5%, the resulting transparent conducting film will have a high resistance, a poor strength and a poor chemical resistance. If the mixing ratio is above 20%, the resistance will be higher, and the film will be harder to etch.

Furthermore, as a result of studies of indium compounds and solvents that can produce a transparent conducting film having the lowest resistance and a high strength when an alkyl tin nitrate was used as the tin compound, it was found that a transparent conducting film having the best characteristics could be obtained when such an indium compound was used as represented by the following general formula:

$$In(NO_3)_p(Y)_q$$

wherein Y is a dicarboxylic acid or a dicarboxylic acid monoester whose one or two protons represented by $\ominus OOC.R'.COOR''$ or $\ominus OOC.R'.COO\ominus$ are dissociated, where R' represents an alkylene group such as $-CH_2CH_2-$, and

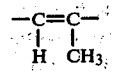

and R'' is H or an alkyl group such as an alkyl group having 1 to 5 carbon atoms, and $p+q=3$ and p or q is an integer of 1 or 2 when Y is $\ominus OOC.R'.COOR''$, and $2p+q=3$ and p or q is an integer of 1 or 2 when Y is $\ominus OOC.R'.COO\ominus$, (the indium compound as defined above will be hereinafter referred to as "indium nitrate dicarboxylate"), and a solvent containing at least 60% by weight of an alcohol or alcohols was used.

This is because a homogeneous mixture of these two compounds is obtained owing to distinguished film-forming property and thermal decomposition property of indium nitrate dicarboxylate and good dissolution of a good solvent for the alkyl tin nitrate so that a transparent conducting film having a uniformly distributed indium and tin and a good compactness can be obtained.

The present invention will be described in detail below, as regards the respective components of the present invention and the process for preparing a transparent conducting film.

The alkyl tin nitrate for use in the present invention is tetravalent tin compounds having at least one each of alkyl groups and nitrate groups, and includes, for example, $(CH_3)Sn(NO_3)_3$, $(CH_3)Sn(NO_3)_2(OH)$, $(CH_3)Sn(NO_3)_2(Cl)$, $(CH_3)Sn(NO_3)_2(OOCC_7H_{15})$, $(CH_3)_2Sn(NO_3)_2$, $(CH_3)_2Sn(NO_3)OH$, $(CH_3)_2Sn(NO_3)(F)$, $(CH_3)_2Sn(NO_3)(OOCC_4H_9)$, $(CH_3)_3Sn(NO_3)$, $(C_2H_5)_2Sn(NO_3)_2$, $(C_3H_5)_2Sn(NO_3)OH$, and $(C_4H_5)_2Sn(NO_3)(OOCC_7H_{15})$, among which $(CH_3)_2Sn(NO_3)_2$ and $(CH_3)_2Sn(NO_3)OH$ are most preferable. These compounds can be used alone or in a mixture of at least two thereof.

These alkyl tin nitrates can be prepared, for example, according to the following reactions:

$(CH_3)Sn(O)(OH) + 3HNO_3 \rightarrow (CH_3)Sn(NO_3)_3 + 2H_2O$ $(CH_3)_2Sn(O) + HNO_3 \rightarrow (CH_3)_2Sn(NO_3)(OH)$ $(C_2H_5)_2Sn(O) + 2HNO_3 \rightarrow (C_2H_5)_2Sn(NO_3)_2 + H_2O$ $(CH_3)_2SnCl_2 + HNO_3 \rightarrow (CH_3)_2Sn(NO_3)(Cl) + HCl$ $(C_4H_9)_2Sn(O) + HNO_3 + C_7H_{15}COOH \rightarrow (C_4H_9)_2Sn(NO_3)(OOCC_7H_{15}) + H_2O$ $(CH_3)_3SnOH + HNO_3 \rightarrow (CH_3)_3Sn(NO_3) + H_2O$ $(CH_3)_3SnOSn(CH_3)_3 + 2HNO_3 \rightarrow 2(CH_3)_3Sn(NO_3) + H_2O$ The foregoing reaction can be carried out in a solvent, and nitric acid can be added in excess when a tin compound having only the alkyl group and the nitrate group, for example, $(CH_3)_3Sn(NO_3)$ is prepared. It is also possible to accelerate the respective reactions by heating. The reaction product alkyl tin nitrate can be isolated by removing the solvent used in the reaction system and the formed water, for example, by evaporating under a reduced pressure, and the isolated product can be used. Alternately, the reaction product solution as such, that is, without such isolation, can be mixed with an indium compound and the solvent to prepare a coating solution.

As the indium compound for use in the present invention, various indium compounds such as indium carboxylate, indium acetylacetonate, alkoxy indium, etc., can be used, and the most preferable compounds are those having both nitrate group and a dicarboxylic acid, represented by the following formula:

$$In(NO_3)_p(OOC.R'.COOR'')_q \text{ or,}$$

$$In(NO_3)_p(OOC.R'.COO)_q$$

where the starting material for the moiety represented by $OOC.R'.COOR''$ or $OOC.R'.COO$ includes, for example, succinic acid, methylsuccinic acid, malonic acid, maleic acid, citraconic acid, itaconic acid and their monoester compounds, among which methylsuccinic acid, citraconic acid, monoethyl methylsuccinate, monoethyl citraconate, etc. are particularly most preferable. These indium compounds can be used alone, or in a mixture of at least two thereof.

These compounds can be prepared, for example, in ethyl alcohol according to the following reactions:

$In(OH)_3 + 2HNO_3 + HOOC.R'.COOR'' \rightarrow In(NO_3)_2(OOC.R'.COOR'') + 3H_2O$ $In(OH)_3 + HNO_3 + HOOC.R'.COOH \rightarrow In(NO_3)(OOC.R'.COO) + 3H_2O$

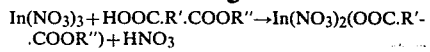

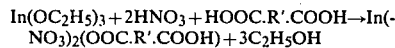

Preferably, these reactions are carried out at a temperature from the ordinary temperature to 60° C. for 3 to 96 hours. The reaction product indium dicarboxylate nitrate can be isolated from the reaction product solution for use in the present coating solution. Alternately, the reaction product solution as such without such isolation can be mixed with an alkyl tin nitrate and a solvent and used in the present coating solution.

As the solvent for use in the present coating solution, alcohols, ketones, esters, and ethers can be used, among which the alcohols are most preferable.

The alcohols include, for example, methyl alcohol, ethyl alcohol, propyl alcohol, isopropyl alcohol, ethyl cellosolve, butyl cellosolve, ethyl carbitol, butyl carbitol, ethylene glycol, propylene glycol, diethylene glycol, etc., and can be used alone or in a mixture of at least two thereof, among which a mixed solution containing 80–98% by weight of ethyl alcohol and 20–2% by weight of ethylene glycol is preferable.

Mixtures of these alcohols with other solvents such as ketones, esters and ethers can be used, but a mixture containing at least 60% by weight of the alcohols is preferable.

A process for preparing a transparent conducting film from the present composition will be described below.

The present composition can be applied to a substrate by dipping, spraying, spinner coating, brush coating, printing, etc. For uniform coating onto a substrate of large area, dipping is particularly suitable. After the coating, drying is carried out, if required, and then firing is carried out to obtain a transparent conducting film.

Firing peak temperature is preferably 400° C. or higher, and a transparent conducting film having a lower resistance can be obtained at a higher peak temperature. When ultraviolet irradition of the coating film is carried out at a substrate temperature of at least about 200° C. before the firing, a film having a lower resistance and a higher strength can be obtained.

BRIEF DESCRIPTION OF THE DRAWING

The single FIGURE shows the relationship between the sheet resistivity of a film and the ratio Sn/(In+Sn) in atomic percent.

DETAILED DESCRIPTION OF THE PREFERRED EMBODIMENTS

The present invention will be described in detail below, referring to Examples.

EXAMPLE 1

100 Parts by weight of ethyl alcohol, 13 parts by weight of fuming nitric acid, and 13 parts by weight of citraconic acid were added to 25 parts by weight of In(OC$_2$H$_5$)$_3$ and stirred at 40° C. for 48 hours to prepare an indium compound solution A.

Separately, 300 parts by weight of ethyl alcohol and 4 parts by weight of methylsuccinic acid were added to 25 parts by weight of In(NO$_3$)$_3$.3H$_2$O, and stirred at 30° C. for 24 hours to prepare an indium compound solution B.

Separately, 6.4 parts by weight of (CH$_3$)Sn(O)OH was added portion-by-portion to a mixed solution of 20 parts by weight of ethyl alcohol and 30 parts by weight of fuming nitric acid and stirred for 5 hours to prepare a tin compound solution a.

Separately, 4 parts by weight of (CH$_3$)$_2$Sn(O) was added portion-by-portion to a mixed solution of 20 parts by weight of ethylene glycol and 8 parts by weight of fuming nitric acid, and stirred for 5 hours to prepare a tin compound solution b.

Seperately, 4 parts by weight of (C$_2$H$_5$)$_2$Sn(O) was added portion-by-portion to a mixed solution of 10 parts by weight of ethyl alcohol and 8 parts by weight of fuming nitric acid, and stirred for 5 hours to prepare a tin compound solution c.

Separately, 2.2 parts by weight of (CH$_3$)$_2$SnCl$_2$ was added portion-by-portion to a mixed solution of 10 parts by weight of ethyl alcohol and one part by weight of fuming nitric acid, and stirred for 5 hours to prepare a tin compound solution d.

Separetely, 2.5 parts by weight of (C$_4$H$_9$)$_2$SnO was added portion-by-portion to a mixed solution of 10 parts by weight of ethyl cellosolve, 3 parts by weight of fuming nitric acid, and 1.5 parts by weight of octylic acid, and stirred for 5 hours to prepare a tin compound solution e.

Separately, 1.8 parts by weight of (CH$_3$)$_3$SnOH was added portion-by-portion to a mixed solution of 10 parts by weight of methyl alcohol and 4 parts by weight of fuming nitric acid, and stirred for 5 hours to prepare a tin compound solution f.

Separately, 2 parts by weight of (CH$_3$)$_3$SnOSn(CH$_3$)$_3$ was added portion-by-portion to a mixed solution of 10 parts by weight of ethyl alcohol and 6 parts by weight of fuming nitric acid and stirred for 5 hours to prepare a tin compound solution g.

The thus prepared tin compound solutions a–g were added to the indium compound solution A in a mixing ratio of 13% in terms of Sn/(In+Sn), and further 2 parts by weight of ethyl alcohol was added to the respective mixtures on the basis of 1.5 parts by weight of the indium compound solution A, and the resulting mixtures were stirred for 5 hours to prepare compositions for preparing a transparent conducting film.

Separately, the tin compound solutions h–j were added to the indium compound solution B in a mixing ratio of 13% in terms of Sn/(In+Sn), and then stirred for 5 hours to prepare compositions for preparing a transparent conducting film.

Then, soda glass substrates each with a 2,000 Å-thick SiO$_2$ film on the adequately cleaned surfaces were dipped in these compositions and then withdrawn at a rate of 30 cm/min. to coat the substrate surfaces with the compositions. The coated substrates were heated to about 350° C. at a temperature-increasing rate of 140° C./min., and at the same time irradiated with ultraviolet rays at an intensity of 200 mW/cm$^2$ (at 254 nm) by means of a metal halide lamp for 5 minutes, then fired at 500° C. for one hour, and annealed at 250° C. for 15 minutes to prepare transparent conducting films.

As shown in the following Table, the resulting transparent conducting films had a mean sheet resistivity of 0.9–1.3 KΩ/□ and a value of mean sheet resistivity plus 3σ of 2 KΩ/□ or less at a film thickness of 450–530 Å. No cracks and no white turbid state were observed in these transparent conducting films, and their mechanical strength was quite satisfactory.

TABLE

| No. | Composition In compound solution | Composition Sn compound solution | Film thickness Å | Characteristics of transparent conducting film Appearance | Sheet resistivity (KΩ/□) R | Sheet resistivity (KΩ/□) R + 3σ | Film strength |
|---|---|---|---|---|---|---|---|
| 1 | A | a | 520 | good | 1.3 | 1.9 | good |
| 2 |   | b | 480 | "    | 0.9 | 1.5 | "    |
| 3 |   | c | 510 | "    | 1.1 | 1.8 | "    |
| 4 |   | d | 460 | "    | 1.2 | 1.7 | "    |
| 5 |   | e | 480 | "    | 1.3 | 2.0 | "    |
| 6 |   | f | 480 | "    | 1.0 | 1.6 | "    |
| 7 |   | g | 530 | "    | 1.1 | 1.8 | "    |
| 8 | B | h | 410 | "    | 1.2 | 1.8 | "    |
| 9 |   | i | 400 | "    | 0.9 | 1.6 | "    |
| 10|   | j | 400 | "    | 1.0 | 1.8 | "    |

EXAMPLE 2

16.6 Parts by weight of In(OH)₃ was added portion-by-portion to a mixed solution of 50 parts by weight of ethyl alcohol, 15 parts by weight of fuming nitric acid, and 15 parts by weight of methylsuccinic acid at 40° C. with stirring for 96 hours, and then 90 parts by weight of ethyl alcohol was added thereto and stirred for 2 hours, with insoluble matters occuring in a small amount being removed by a teflon filter to prepare an indium compound solution C.

The tin compound solution b shown in Table, No. 2 was added to the resulting indium compound solution C in various mixing ratio to prepare compositions for preparing a transparent conducting film in Sn/(In+Sn) of 5-20%.

Transparent conducting films were prepared from these compositions in the same manner as in Example 1 and characteristics of the resulting films were investigated. The relations between the sheet resistivity of the films and Sn/(In+Sn) are as shown in FIGURE, from which it is obvious that the lowest resistance is obtained in Sn/(In+Sn) of about 13%, and a practical conducting film can be obtained in Sn/(In+Sn) of 5-20%.

In Sn/(In+Sn) of less than 5%, the film has a poor strength and a poor chemical resistance, and in Sn/(In+Sn) of more than 20%, the film has a poor etching susceptibility by an etching solution of HCl system.

EXAMPLE 3

Compositions of Table, Nos. 1-10 were preserved at room temperature and 40° C. for about 60 days, and transparent conducting films were prepared periodically within the said period of 60 days from the preserved compositions to trace changes in film characteristics. The thus prepared transparent conducting films had no differences in appearance, light transmission, sheet resistivity, chemical resistance and etching susceptibility from those of the transparent conducting films prepared from the compositions right after their preparation.

However, when compositions containing other tin compounds than those of the present invention, for example, tin octylate and stannous chloride were preserved at room temperature for about 30 days and at 40° C. for about 10 days, the transparent conducting sheets prepared from such preserved compositions had a high sheet resistivity and a low strength and a low chemical resistance.

As described above, a transparent, conducting film having a low resistance (sheet resistivity of about 1 KΩ/□ at a film thickness of 500 Å), and distinguished mechanical strength, chemical resistance and etching susceptibility from the present composition according to the present process for preparing a transparent conducting film, the process being several times as productive as the conventional electron beam vapor deposition process, etc.

The present composition has a long pot life. For example, in the coating by dipping, a large volume of the composition is used for one batch, but the frequency of exchanging one batch can be reduced to less than one-half of the conventional one, so that the expensive composition can be effectively utilized. Furthermore, the characteristics of a transparent conducting film can be stably maintained.

What is claimed is:

1. A composition for preparing a transparent conducting film, which comprises an indium compound, a tin compound, and a solvent as essential components, the tin compound being a compound represented by the following general formula:

$$(R)_a Sn(NO_3)_b (X)_{4-a-b} \qquad (1)$$

wherein R is an alkyl group having 1 to 4 carbon atoms, X is a hydroxyl group, a halogen atom, or a carboxyl group, and a and b are integers of 1~3 and a+b≦4, the indium compound and the tin compound represented by the general formula (1) being in a mixing ratio of the indium compound to the indium compound plus the tin compound of 5-20% by weight in terms of Sn/(In+Sn)×100, and total of the indium compound and the tin compound represented by the general formula (1), and the solvent being in a proportion of 2 to 80% by weight of the total of the indium compound and the tin compound represented by the general formula (1) and 98 to 20% by weight of the solvent.

2. The composition according to claim 1, wherein the indium compound is a compound represented by In(NO₃)$_p$(Y)$_q$, where Y is a dicarboxylic acid or dicarboxylic acid monoester whose one or two protons are dissociated, represented by ⊖OOC.R'.COOR" or ⊖OOC.R'.COO⊖, where R' represents an alkylene group, and R" is H or an alkyl group, and p+q=3 and p or q is an integer of 1 or 2 when Y is ⊖OOC.R'.COOR" and 2p+q=3 and p or q is an integer of 1 or 2 when Y is ⊖OOC.R'.COO⊖.

3. A process for preparing a transparent conducting film, which comprises coating a substrate with a composition comprising an indium compound, a tin compound, and a solvent as essential components, the tin compound being a compound represented by the following general formula:

$$(R)_aSn(NO_3)_b(X)_{4-a-b} \quad (1)$$

wherein R is an alkyl group having 1 to 4 carbon atoms, X is a hydroxyl group, a halogen atom or a carboxyl group, and a and b are integers of 1~3 and a+b≦4, the indium compound and the tin compound represented by the general formula (1) being in a mixing ratio of the indium compound to the indium compound plus the tin compound of 5-20% by weight in terms of Sn/(In+Sn)×100, and total of the indium compound and the tin compound represented by the general formula (1), and the solvent being in a proportion of 2 to 80% by weight of the total of the indium compound and the tin compound represented by the general formula (1) and 98 to 20% by weight of the solvent, subjecting the coated substrate to at least one of drying and ultraviolet irradiation at a substrate temperature of 200° C. or higher, when required, and then heating the substrate at a temperature of 400° C. or higher.

4. The process according to claim 3, wherein the indium compound is a compound represented by $In(NO_3)_p(Y)_q$, where Y is a dicarboxylic acid or dicarboxylic acid monoester whose one or two protons are dissociated, represented by $\ominus OOC.R'.COOR''$ or $\ominus OOC.R'.COO\ominus$, where R' represents alkyl group, and R'' is H or an alkyl group, and p+q=3 and p or q is an integer of 1 or 2 when Y is $\ominus OOC.R'.COOR''$, and 2p+q=3 and p or q an integer of 1 or 2 when Y is $\ominus OOC.R'.COO\ominus$, the solvent consists of 80 to 98% by weight of ethyl alcohol and 20 to 2% by weight of ethylene glycol, and the tin compound represented by the general formula (1) is at least one of $(CH_3)_2Sn(NO_3)_2$ and $(CH_3)_2Sn(NO_3)OH$.

5. The composition according to claim 1, wherein the indium compound and the tin compound are in a mixing ratio of 8-15 wt.% in terms of Sn/(In+Sn)×100.

6. The compound according to claim 1, wherein the tin compound is at least one of $(CH_3)Sn(NO_3)_3$, $(CH_3)Sn(NO_3)_2(OH)$, $(CH_3)Sn(NO_3)_2(Cl)$, $(CH_3)Sn(NO_3)_2(OOCC_7H_{15})$, $(CH_3)_2Sn(NO_3)_2$, $(CH_3)_2Sn(NO_3)OH$, $(CH_3)_2Sn(NO_3)(F)$, $(CH_3)_2Sn(NO_3)(OOCC_4H_9)$, $(CH_3)_3Sn(NO_3)$, $(C_2H_5)_2Sn(NO_3)_2$, $(C_3H_5)_2Sn(NO_3)(OH)$, and $(C_4H_5)_2Sn(NO_3)(OOCC_7H_{15})$.

7. The composition according to claim 1, wherein the solvent is at least one alcohol or a mixture containing at least 60 wt.% of an alcohol and at least one solvent selected from the group consisting of ketone, an ester and an ether.

8. The composition according to claim 1, wherein the solvent consists of 80-98 wt.% of ethyl alcohol and 20-2 wt.% of ethyleneglycol.

9. The composition according to claim 1, wherein the tin compound is at least one of $(CH_3)_2Sn(NO_3)_2$ and $(CH_3)_2Sn(NO_3)(OH)$, and Sn/(In+Sn) is 8-15 wt.%, and the solvent consists of 80-98 wt.% of ethyl alcohol and 20-2 wt.% of ethyleneglycol.

10. The composition according to claim 2, wherein the indium compound and the tin compound are in a mixing ratio of 8-15 wt.% in terms of Sn/(In+Sn)×100.

11. The composition according to claim 2, wherein the tin compound is at least one of $(CH_3)Sn(NO_3)_3$, $(CH_3)Sn(NO_3)_2(OH)$, $(CH_3)Sn(NO_3)_2(Cl)$, $(CH_3)Sn(NO_3)_2(OOCC_7H_{15})$, $(CH_3)_2Sn(NO_3)_2$, $(CH_3)_2Sn(NO_3)OH$, $(CH_3)_2Sn(NO_3)(F)$, $(CH_3)_2Sn(NO_3)(OOCC_4H_9)$, $(CH_3)_3Sn(NO_3)$, $(C_2H_5)_2Sn(NO_3)_2$, $(C_3H_5)_2Sn(NO_3)(OH)$ and $(C_4H_5)_2Sn(NO_3)(OOCC_7H_{15})$.

12. The composition according to claim 2, wherein Y in $In(NO_3)_p(Y)_q$ is succinic acid, methylsuccinic acid, malonic acid, maleic acid, citraconic acid, intaconic acid or their monoester.

13. The composition accord to claim 2, wherein the solvent is at least one alcohol or a mixture containing at least 60 wt.% of an alcohol and at least one solvent selected from the group consisting of a ketone, an ester and an ether.

14. The composition according to claim 2, wherein the solvent consists of 80-98 wt.% of ethyl alcohol and 20-2 wt.% of ethyleneglycol.

15. The composition according to claim 2, wherein the tin compound is at least one of $(CH_3)_2Sn(NO_3)_2$ and $(CH_3)_2Sn(NO_3)(OH)$, and Sn/(In+Sn) is 8-15 wt.%, the solvent consists of 80-98 wt.% of ethyl alcohol and 20-2 Wt.% of ethyleneglycol, and Y is methyl-succinic acid, citraconic acid, monomethyl methylsuccinate or monoethyl citraconate.

16. The process according to claim 3, wherein the indium compound and the tin compound are in a mixing ratio of 8-15 wt.% in terms of Sn/(In+Sn)×100.

17. The process according to claim 3, wherein the tin compound is at least one of $(CH_3)Sn(NO_3)_3$, $(CH_3)Sn(NO_3)_2(OH)$, $(CH_3)Sn(NO_3)_2(Cl)$, $(CH_3)Sn(NO_3)_2(OOCC_7H_{15})$, $(CH_3)_2Sn(NO_3)_2$, $(CH_3)_2Sn(NO_3)OH$, $(CH_3)_2Sn(NO_3)(F)$, $(CH_3)_2Sn(NO_3)(OOCC_4H_9)$, $(CH_3)_3Sn(NO_3)$, $(C_2H_5)_2Sn(NO_3)_2$, $(C_3H_5)_2Sn(NO_3)(OH)$, and $(C_4H_5)_2Sn(NO_3)(OOCC_7H_{15})$.

18. The process according to claim 3, wherein the solvent is at least one alcohol or a mixture containing at least 60 wt.% of an alcohol and at least one solvent from the group consisting of a ketone, an ester and an ether.

19. The process according to claim 3, wherein the solvent consists of 80-98 wt.% of ethyl alcohol and 20-2 wt.% of ethyleneglycol.

20. The process according to claim 3, wherein the tin compound is at least one of $(CH_3)_2Sn(NO_3)_2$ and $(CH_3)_2Sn(NO_3)(OH)$, and Sn/(In+Sn) is 8-15 wt.%, and the solvent consists of 80-98 wt.% of ethyl alcohol and 20-2 wt.% of ethyleneglycol.

21. The process according to claim 1, wherein the indium compound is a compound represented by $In(NO_3)_p(Y)_q$, where Y is a dicarboxylic acid or dicarboxylic acid monether whose one or two protons are dissociated, represented by $\ominus OOC.R'.COOR''$ or $\ominus OOC.R'.COO\ominus$, where R' represents an alkylene group, and R'' is H or an alkyl group, and p+q=3 and p or q is an integer of 1 or 2 when Y is $\ominus OOC.R'.COOR''$ and 2p+q=3 and p or q is an integer of 1 or 2 when Y is $\ominus OOC.R'.COO\ominus$.

22. The process according to claim 21, wherein the indium compound and the tin compound are in a mixing ratio of 8-15 wt.% in terms of Sn/(In+Sn)×100.

23. The process according to claim 21, wherein the tin compound is at least one of $(CH_3)Sn(NO_3)_3$, $(CH_3)Sn(NO_3)_2(OH)$, $(CH_3)Sn(NO_3)_2(Cl)$, $(CH_3)Sn(NO_3)_2(OOCC_7H_{15})$, $(CH_3)_2Sn(NO_3)_2$, $(CH_3)_2Sn(NO_3)OH$, $(CH_3)_2Sn(NO_3)(F)$, $(CH_3)_2Sn(NO_3)(OOCC_4H_9)$, $(CH_3)_3Sn(NO_3)$, $(C_2H_5)_2Sn(NO_3)_2$, $(C_3H_5)_2Sn(NO_3)(OH)$ and $(C_4H_5)_2Sn(NO_3)(OOCC_7H_{15})$.

24. The process according to claim 21, wherein Y in $In(NO_3)_p(Y)_q$ is succinic acid, methylsuccinic acid, malonic acid, maleic acid, citraconic acid, intaconic acid or their monoester.

25. The process according to claim 21, wherein the solvent is an alcohol or contains at least 60 wt.% of an alcohol.

26. The process according to claim 21, wherein the solvent consists of 80–98 wt.% of ethyl alcohol and 20–2 wt.% of ethyleneglycol.

27. The process according to claim 21, wherein the tin compound is at least one of $(CH_3)_2Sn(NO_3)_2$ and $(CH_3)_2Sn(NO_3)(OH)$, and Sn/(In+Sn) is 8–15 wt.%, the solvent consists of 80–98 wt.% of ethyl alcohol and 20–2 wt.% of ethyleneglycol, and Y is methyl-succinic acid, citraconic acid, monomethyl methylsuccinate or monoethyl citraconate.

* * * * *